United States Patent
Stevens et al.

(10) Patent No.: US 12,370,284 B2
(45) Date of Patent: Jul. 29, 2025

(54) ANTIMICROBIAL ADHESIVE COPOLYMER COMPOSITIONS

(71) Applicant: Rhianna Pauline Stevens, Brighton, MA (US)

(72) Inventors: Rhianna Pauline Stevens, Brighton, MA (US); Emma Jenkins, Brighton, MA (US)

( * ) Notice: Subject to any disclaimer, the term of this patent is extended or adjusted under 35 U.S.C. 154(b) by 1035 days.

(21) Appl. No.: 17/242,241

(22) Filed: Apr. 27, 2021

(65) Prior Publication Data

US 2021/0330857 A1    Oct. 28, 2021

Related U.S. Application Data

(60) Provisional application No. 63/101,354, filed on Apr. 27, 2020.

(51) Int. Cl.
| | | |
|---|---|---|
| *A61L 24/00* | (2006.01) | |
| *A61L 24/04* | (2006.01) | |
| *C08F 220/34* | (2006.01) | |
| *C08K 5/19* | (2006.01) | |
| *C08K 5/315* | (2006.01) | |
| *C08K 5/50* | (2006.01) | |

(52) U.S. Cl.
CPC ......... *A61L 24/0015* (2013.01); *A61L 24/046* (2013.01); *C08F 220/34* (2013.01); *C08K 5/19* (2013.01); *C08K 5/315* (2013.01); *C08K 5/50* (2013.01); *A61L 2300/404* (2013.01)

(58) Field of Classification Search
CPC .............. A61L 24/0015; A61L 24/046; A61L 2300/404; C08F 220/34; C08K 5/19; C08K 5/315; C08K 5/50
See application file for complete search history.

(56) References Cited

U.S. PATENT DOCUMENTS

| | | | | |
|---|---|---|---|---|
| 5,403,505 A | * | 4/1995 | Hachmann | C11D 3/48 422/16 |
| 2016/0015373 A1 | * | 1/2016 | Russo | A61B 17/00491 401/268 |
| 2018/0368401 A1 | * | 12/2018 | Swamy | A01N 43/16 |

* cited by examiner

*Primary Examiner* — Blessing M Fubara
(74) *Attorney, Agent, or Firm* — Law Office of Matthew M. Yospin; Matthew M. Yospin

(57) ABSTRACT

Improved antimicrobial adhesive copolymer compositions for wound closure or surgical-site closure are provided. The antimicrobial adhesive copolymer compositions comprise cyanoacrylate-based tissue adhesive monomers and long-chain quaternary ammonium compounds (QUATs), or long-chain quaternary phosphonium compounds (QUPTs). The antimicrobial adhesive copolymer compositions offer advantages in wound closure or surgical-site closure with bactericidal and bacteriostatic effects on Gram-positive and Gram-negative organisms.

10 Claims, 10 Drawing Sheets

Chemical reaction for auto-polymerization of cyanoacrylates.

n = 8, 10, 12, 14, 16, 18

Chemical structure of benzalkonium chloride.

n = 8, 10, 12, 14, 16, 18

Chemical structure of (vinylbenzyl)dimethyl alkyl ammonium chloride.

Proton nuclear magnetic resonance spectroscopy data for the sample of 0.2% QUAT copolymer.

Proton nuclear magnetic resonance spectroscopy data for the sample of 2.0% QUAT copolymer.

| Peak | Int. Value: 0.2% QUAT | Int. Value: 2.0% QUAT |
|---|---|---|
| A | 001.00 | 001.00 |
| B | 120.03 | 025.92 |
| C | 000.62 | 000.64 |
| Actual QUAT presence | 0.13% | 0.62% |
| % Yield (est) | 65.0% | 31.0% |

FIG. 4

Average absorbance of samples from all assays using an ultraviolet–visible spectrophotometer at 600 nm.

| Absorbance at 600nm (AU) (Average of 9 total assays) | | |
|---|---|---|
| Sample | E. coli | S. epidermidis |
| Control | 0.689 | 0.813 |
| Cyanoacrylate only | 0.665 | 0.537 |
| 0.2% QUAT | 0.330 | 0.184 |
| 0.5% QUAT | 0.074 | 0.065 |
| 2.0% QUAT | 0.067 | 0.061 |
| 5.0% QUAT | 0.081 | 0.080 |

FIG. 6

S. epidermidis (control, no polymer)

S. epidermidis (0.0% QUAT)

S. epidermidis (0.2% QUAT)

S. epidermidis (0.5% QUAT)

S. epidermidis (2.0% QUAT)

S. epidermidis (5.0% QUAT)

E. coli (control, no polymer)

E. coli (0.0% QUAT)

E. coli (0.2% QUAT)

E. coli (0.5% QUAT)

E. coli (2.0% QUAT)

E. coli (5.0% QUAT)

ANTIMICROBIAL ADHESIVE COPOLYMER COMPOSITIONS

FIELD OF THE INVENTION

The presently disclosed subject matter relates to antimicrobial adhesives, and more particularly, to antimicrobial adhesive copolymer compositions for wound closure or surgical site closure.

BACKGROUND OF THE INVENTION

Non-toxic adhesive compounds, particularly 2-octyl cyanoacrylate ("2oc"), are well known for use in medical and surgical applications for wound closure and surgical site closure. The use of cyanoacrylate polymer for wound closure has been shown to provide greater protection against surgical site infections when compared to staples. The adhesive property of these compounds stems from the mechanism by which they polymerize rapidly upon contact with skin. Typical auto-polymerization of cyanoacrylates occurs via an anionic mechanism. Infections continue to be a leading cause of post-operative death: as much as one-third of post-operative deaths are due to infections, with 12% of patients in low-to-middle-income countries and 2% of patients in the U.S. experiencing surgical-site infections (B. Allegranzi, et al., Lancet Infect. Dis. 2016, 16, e276; B. Allegranzi, et al., Lancet Infect. Dis. 2016, 16, e288).

While useful in prevention of subsequent infections, in the case of a wound that is already contaminated, these adhesives may seal pathogenic bacteria inside the wound bed. The polymer does not demonstrate sufficient antibacterial properties on its own. Using it to seal a wound that has already been contaminated, for instance trauma wounds including abrasions, lacerations, crush wounds, penetration and puncture wounds, is contraindicated due to the possibility of trapping microbial pathogens beneath the tissue.

Several attempts to introduce antimicrobial properties to these adhesives have been reported—see, e.g., B. Allegranzi, et al., Lancet Infect. Dis. 2016, 16, e276; B. Allegranzi, et al., Lancet Infect. Dis. 2016, 16, e288; M. Ando, et al., Eur. Spine J. 2014, 23, 854; K. A. Ban, et al., J. Am. Coll. Surg. 2017, 224, 59; G. Daeschlein, et al., Int. J. Infect. Diseases 2014, 29, 274; N.A. World Health Organization's Global Guidelines for the Prevention of Surgical Site Infection. 2016. Promising approaches have used polyvinyl alcohol polymer as a base, with additions of gelatin, plant extracts, or carbon nanotubes to enhance antibacterial and mechanical properties—see S. M. M. Dadfar, G. Kavoosi, S. M. A. Dadfar, Polym. Compos. 2014, 35, 1736; G. Kavoosi, et al., J. Appl. Polym. Sci. 2017, 134, 45341.

Quaternary ammonium compounds ("QUATs") are long-chain positively charged polyatomic ions in which the central atom is N+ and its four covalently attached side chains are alkyl or aryl in nature. QUATs, as a class, are well-known and consistently effective as antimicrobial molecules. Benzalkonium chlorides ("BACs") are common and widely available as antimicrobial agents, present in commercial disinfectant brands and many other all-purpose household cleaners. BACs are favored because of their broad antimicrobial properties against a variety of bacteria, viruses, and fungi. BACs are highly water-soluble, very stable, and demonstrate relatively low toxicity to humans, making them safe for everyday use. The general chemical structure of BACs is depicted in FIG. 2A. The use of QUATs in wound care has been explored with materials other than cyanoacrylates, such as a wound dressing consisting of chitin and QUATs (see D. Zhou, R. Yang, T. Yang, M. Xing, G. Luo, Int. J. Nanomed. 2018, 13, 4157), and a nanocomposite consisting of graphene oxide as a two-dimensional, one atom-thick sheet composed of sp2-hybridized carbon atoms and QUATs (see T. Liu, Y. Liu, M. Liu, Y. Wang, W. He, G. Shi, X. Hu, R. Zhan, G. Luo, M. Xing, J. Wu, Burns Trauma 2018, 6, 16) to be applied topically or incorporated into dressings, but it lacks stability in aqueous solutions.

While known prior art shows promise for introducing antimicrobial properties to adhesives, the known art does not incorporate broad-spectrum antimicrobial compounds into co-polymers that can be safely used with polymers for wound closure. Currently, there exists no successful method for closing contaminated wounds without the need for additional treatments to prevent infection. A need exists for antimicrobial adhesive copolymer compounds that are effective against a range of microbial contaminants, including bacteria, viruses, and fungi, and which are stable and non-to initial consultation to humans. A need exists for antimicrobial adhesive copolymer compositions which may be used in already-contaminated wounds and which will effectively kill bacteria.

SUMMARY OF THE INVENTION

The present disclosure meets these needs, by disclosing antimicrobial adhesive copolymer compositions for wound closure, which encompasses surgical site closure, specifically a copolymer comprising cyanoacrylate-based tissue adhesive monomers and long-chain quaternary ammonium compounds (QUATs). QUATs contain a positively charged central nitrogen atom (N+) which attracts the negatively charged outer membranes of bacteria. This mechanism causes the long hydrophobic chain of the QUAT to pierce the bacterial cell membrane, lysing the bacterial cell.

While the antimicrobial properties of BACs are highly effective, the compounds lack the necessary vinyl group or similar reaction site for formation of covalent 2oc-BAC bonds. As depicted in FIG. 1, cyanoacrylates polymerize via an anionic mechanism, attacking the target monomer at the site of an alkene and repeating this cascade of reactions. In order for this mechanism to be exploited for the incorporation of an antimicrobial agent, that agent must comprise a reactive alkene, such as a vinyl group. A potential option is (vinylbenzyl) dimethyl alkyl ammonium chloride molecule ("VBA"). These compounds are nearly identical in structure and function to BACs, with the addition of a vinyl group in the para position relative to the dimethyl alkyl ammonium group (FIG. 2B). This vinyl group provides an ideal site for a mechanism of polymerization similar to that of cyanoacrylates. These compounds have previously been used successfully in copolymers with vinylbenzyl thymine to create antimicrobial surface coatings.

The present disclosure describes antimicrobial adhesive copolymer compositions comprising varying relative concentrations of QUAT monomers and 2-octyl cyanoacrylate (2oc) monomers. The present disclosure teaches antimicrobial adhesive copolymer compositions comprising covalent incorporation of QUAT monomers into a compatible, antibacterial, cyanoacrylate-based polymer. Incorporating QUATs into the cyanoacrylate-based polymers yields antimicrobial adhesive copolymer compositions which become antimicrobial through a mechanism which is not dependent on diffusion, and which copolymer compositions are effective against both Gram-positive and Gram-negative organisms.

In one aspect, the present disclosure comprises an antimicrobial adhesive copolymer composition for wound closure, comprising: a cyanoacrylate component; and a charged quaternary ammonium component or a charged quaternary phosphonium component, wherein the charged quaternary ammonium component or the charged quaternary phosphonium component comprises at least one reactive alkene group.

In one aspect, the present disclosure comprises an antimicrobial adhesive copolymer composition for wound closure, wherein a cyanoacrylate component is selected from a group comprising methyl cyanoacrylates, ethyl cyanoacrylates, butyl cyanoacrylates, and octyl cyanoacrylates, their derivatives, and mixtures thereof.

In one aspect, the present disclosure comprises an antimicrobial adhesive copolymer composition for wound closure, wherein at least one reactive alkene group comprises at least one vinyl group.

In one aspect, the present disclosure comprises an antimicrobial adhesive copolymer composition for wound closure, wherein the charged quaternary ammonium component is selected from a group comprising (vinylbenzyl)dimethylalkylammonium chloride, (vinylbenzyl)trimethylammonium chloride, trimethyl(vinyl)ammonium chloride, and dimethylalkyl(vinyl)ammonium chloride, their derivatives, and mixtures thereof.

In one aspect, the present disclosure comprises an antimicrobial adhesive copolymer composition for wound closure, wherein the charged quaternary phosphonium component is selected from a group comprising triphenyl(4-vinylbenzyl)phosphonium chloride, tri-n-butyl(4-vinylbenzyl)phosphonium chloride, benzyl(vinyl)phosphonium chloride, trimethyl(4-vinylbenzyl)phosphonium chloride, and (formylmethyl)triphenylphosphonium chloride, their derivatives, and mixtures thereof.

In one aspect, the present disclosure comprises an antimicrobial adhesive copolymer composition for wound closure, wherein the antimicrobial adhesive copolymer composition further comprises one or more of a plurality of charged quaternary ammonium components and/or one or more of a plurality of charged quaternary phosphonium components.

In one aspect, the present disclosure comprises an antimicrobial adhesive copolymer composition for wound closure, wherein a ratio of the cyanoacrylate component to the charged quaternary ammonium component or the charged quaternary phosphonium component is in a range of approximately 99.95% by mole cyanoacrylate component to 0.05% by mole charged quaternary ammonium component or charged quaternary phosphonium component, to approximately 90.0% by mole cyanoacrylate component to 10% by charged quaternary ammonium component or charged quaternary phosphonium component.

In one aspect, the present disclosure comprises an antimicrobial adhesive copolymer composition for wound closure, comprising a chemical component resulting from a reaction between a formaldehyde component and a cyanoacetate component or a cyanoacetic acid component; and a charged quaternary ammonium component or a charged quaternary phosphonium component, wherein the charged quaternary ammonium component or the charged quaternary phosphonium component comprises at least one reactive alkene group.

In one aspect, the present disclosure comprises an antimicrobial adhesive copolymer composition for wound closure, wherein the chemical component resulting from the reaction between the formaldehyde component and the cyanoacetate component or the cyanoacetic acid component comprises one or more members of a group comprising methyl cyanoacrylates, ethyl cyanoacrylates, butyl cyanoacrylates, and octyl cyanoacrylates, their derivatives, and mixtures thereof.

In one aspect, the present disclosure comprises an antimicrobial adhesive copolymer composition for wound closure, wherein the at least one reactive alkene group comprises at least one vinyl group.

In one aspect, the present disclosure comprises an antimicrobial adhesive copolymer composition for wound closure, wherein the charged quaternary ammonium component is selected from a group comprising (vinylbenzyl)dimethylalkylammonium chloride, (vinylbenzyl)trimethylammonium chloride, trimethyl(vinyl)ammonium chloride, and dimethylalkyl(vinyl)ammonium chloride, their derivatives, and mixtures thereof.

In one aspect, the present disclosure comprises an antimicrobial adhesive copolymer composition for wound closure, wherein the charged quaternary phosphonium component is selected from a group comprising triphenyl(4-vinylbenzyl)phosphonium chloride, tri-n-butyl(4-vinylbenzyl)phosphonium chloride, benzyl(vinyl)phosphonium chloride, trimethyl(4-vinylbenzyl)phosphonium chloride, and (formylmethyl)triphenylphosphonium chloride, their derivatives, and mixtures thereof.

In one aspect, the present disclosure comprises an antimicrobial adhesive copolymer composition for wound closure, wherein the antimicrobial adhesive copolymer composition further comprises one or more of a plurality of charged quaternary ammonium components and/or one or more of a plurality of charged quaternary phosphonium components.

In one aspect, the present disclosure comprises an antimicrobial adhesive copolymer composition for wound closure, wherein a ratio of the chemical component (CAC) resulting from the reaction between the formaldehyde component and the cyanoacetate component or the cyanoacetic acid component to the charged quaternary ammonium component or the charged quaternary phosphonium component is in a range of approximately 99.95% by mole CAC to 0.05% by mole charged quaternary ammonium component or charged quaternary phosphonium component, to approximately 90.0% by mole CAC to 10% by charged quaternary ammonium component or charged quaternary phosphonium component.

In one aspect, the present disclosure comprises a method for treatment or prevention of infection at a wound site or a surgical site, the method comprising adhering the wound site or the surgical site closed or partially closed with, or injecting or placing into the wound site or the surgical site, a chemical solution comprising i) a cyanoacrylate component, or a chemical component resulting from a reaction between a) a formaldehyde component and b) any cyanoacetate component or a cyanoacetic acid component; and ii) a charged quaternary ammonium component or a charged quaternary phosphonium component.

In one aspect, the present disclosure comprises a method for treatment or prevention of infection at a wound site or a surgical site, in which the chemical solution comprises a plurality of charged quaternary ammonium components and/or a plurality of charged quaternary phosphonium components.

These aspects of the present disclosure, and others disclosed in the Detailed Description of the Drawings, represent improvements on the current art. This summary is provided to introduce a selection of concepts in a simplified form that are further described below in the Detailed Description of the Preferred Aspects of the present disclosure. This Summary is not intended to identify key features or essential features of the claimed subject matter, nor is it intended to be used to limit the scope of the claimed subject matter.

BRIEF DESCRIPTION OF THE DRAWINGS

The foregoing summary, as well as the following detailed description of various aspects, is better understood when read in conjunction with the appended drawings. For the purposes of illustration, there is shown in the drawings exemplary aspects and relevant background information; but the presently disclosed subject matter is not limited to the specific methods and instrumentalities disclosed. In the following detailed description, various aspects of the present disclosure are described with reference to the following drawings, in which:

FIG. 4 presents a table with data on the ratios of the monomers in the polymers.

FIG. 6 presents a table with data on the average absorbance of samples from the assays using an ultraviolet-visible spectrophotometer at 600 nm.

DESCRIPTION OF THE PREFERRED ASPECTS

Reference is made in detail to the presently preferred aspects of the disclosure. The presently disclosed disclosure is described with specificity to meet statutory requirements. But, the description itself is not intended to limit the scope of this patent. Rather, the claimed disclosure might also be presented in other aspects, to include different steps or elements similar to the ones described in this document, in conjunction with other present or future technologies. Moreover, although the term "step" may be used herein to connote different aspects of methods employed, the term should not be interpreted as implying any particular order among or between various steps herein disclosed unless and except when the order of individual steps is explicitly described. The word "approximately" as used herein means within 5% of a stated value, and for ranges as given, applies to both the start and end of the range of values given, except as otherwise specified.

In the following description, numerous specific details are set forth to provide a thorough understanding of the disclosure. But, the present disclosure may be practiced without these specific details. Structures and techniques that would be known to one of ordinary skill in the art have not been shown in detail, in order not to obscure the disclosure. Referring to the figures, it is possible to see the elements and effects of the antimicrobial adhesive copolymer compositions of the present disclosure.

The present subject matter discloses antimicrobial adhesive copolymer compositions. At a high level of overview, the antimicrobial adhesive copolymer compositions comprise a cyanoacrylate component, or any chemical component resulting from a reaction between a formaldehyde component and any cyanoacetate or cyanoacetic acid component; and a charged quaternary ammonium component, or a charged quaternary phosphonium component, wherein the quaternary ammonium component or quaternary phosphonium component contains at least one vinyl group.

Figure 1:
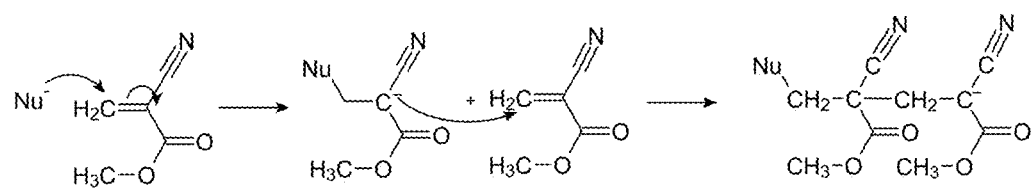
FIG. 1 illustrates a chemical reaction for auto-polymerization of cyanoacrylates.

With reference to FIG. 1, a mechanism for auto-polymerization of cyanoacrylates is shown. The nucleophile is typically an amino acid or a hydroxide ion. Initiation occurs when the nucleophile attacks the vinylic carbon, breaking the vinylic bond and thus generating an anionic charge on the central carbon atom of the cyanoacrylate monomer. This central carbon atom then acts as a nucleophile, inducing a chain of nucleophilic attacks on the remaining cyanoacrylate monomers.

Figure 2A:
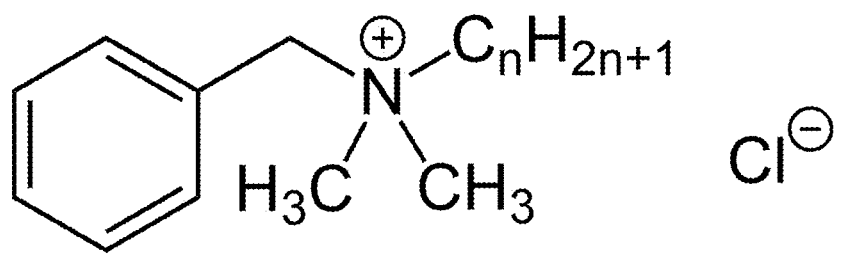
FIG. 2A illustrates the chemical structure of benzalkonium chloride.

With reference to FIG. 2A, the general chemical structure of benzalkonium chloride is depicted. BACs do not necessarily contain a reactive alkene. The aromatic ring helps to stabilize the positive charge on the central nitrogen atom, allowing it to maintain four covalent bonds.

Figure 2B:
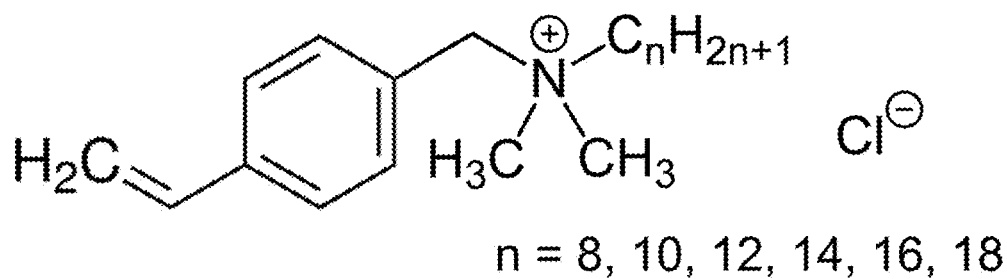
FIG. 2B illustrates the chemical structure of (vinylbenzyl) dimethyl alkyl ammonium chloride.

Cyanoacrylates polymerize via an anionic mechanism, attacking the target monomer at the site of an alkene and repeating this cascade of reactions. In order for this mechanism to be exploited for the incorporation of an antimicrobial agent, that antimicrobial agent must contain a reactive alkene, such as a group. A potential option would be a (vinylbenzyl) dimethyl alkyl ammonium chloride molecule ("VBA"). These compounds are nearly identical in structure and function to BACs, with the addition of a vinyl group in the para position relative to the dimethyl alkyl ammonium group. With reference to FIG. 2B, the chemical structure of (vinylbenzyl)dimethyl alkyl ammonium chloride is depicted. Most antimicrobial compounds possess a longer hydrocarbon chain-often 8 to 16 carbon atoms in length.

The present disclosure teaches a copolymer comprising cyanoacrylate-based tissue adhesive monomers and long-chain QUATs, which contain a positively charged central nitrogen atom which attracts the negatively charged outer membranes of bacteria. This mechanism leads to the long hydrophobic chain of the QUAT piercing bacterial cell membranes, lysing the bacterial cell. Due to the QUAT's ability to kill bacteria, a QUAT and cyanoacrylate copolymer can assist in preventing the development and/or spread of bacterial infection.

Synthesis of the QUAT for the antimicrobial adhesive copolymer compositions material was conducted via a nucleophilic substitution reaction using equal parts dimethyloctylamine (MW 157.30 g/mol) and vinylbenzyl chloride (MW 152.6 g/mol) by mole. The reactants were mixed and stirred at room temperature for at least 24 hours, then soaked in diethyl ether to absorb impurities, and dried via vacuum filtration. This process was repeated until thin-layer chromatography confirmed the purity of the QUAT. The product continued drying under vacuum overnight and was transferred to a pre-weighted vial for storage at room temperature. A QUAT stock solution containing 50 mg QUAT per 1 ml distilled water was created.

The antimicrobial adhesive copolymer compositions comprise varying concentrations between QUAT monomer and 2-octyl cyanoacrylate (2oc) monomer. The antimicrobial adhesive copolymer compositions were prepared by first adding the desired amount of QUAT stock solution to a reaction vessel. Liquid monomeric 2oc was then pipetted into the reaction vessel, and the vessel was agitated gently for 2-5 seconds and then placed on a flat surface, at which point the mixture solidified. The reaction was exothermic and resulted in a translucent solid, with lower QUAT concentrations corresponding to a more transparent polymer product. The antimicrobial adhesive copolymer compositions were labeled, covered, and stored at room temperature.

Figure 3A:
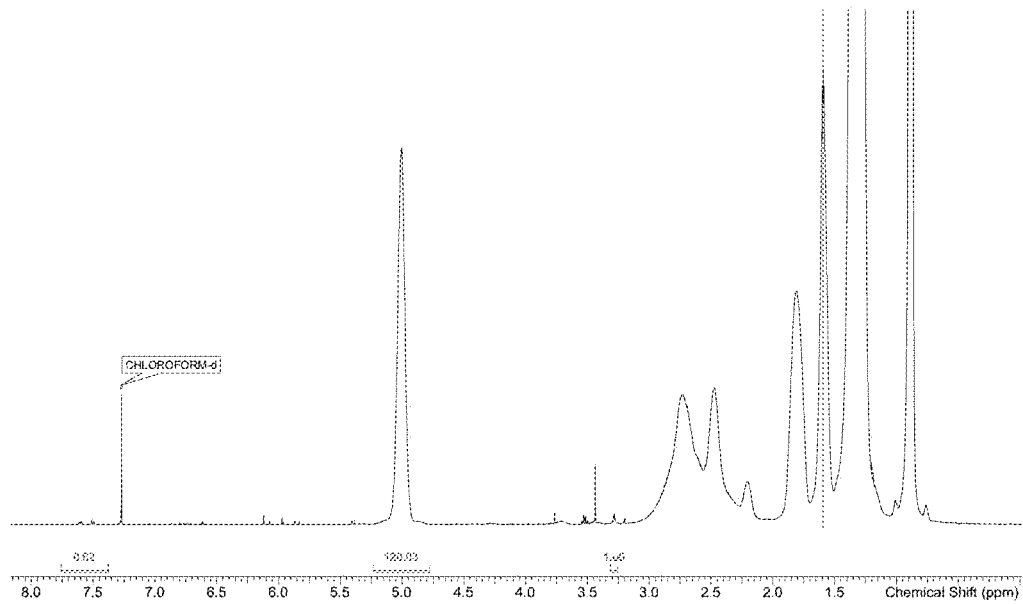
FIG. 3A illustrates the proton nuclear magnetic resonance spectroscopy data for the sample of 0.2% QUAT copolymer.
Figure 3B:
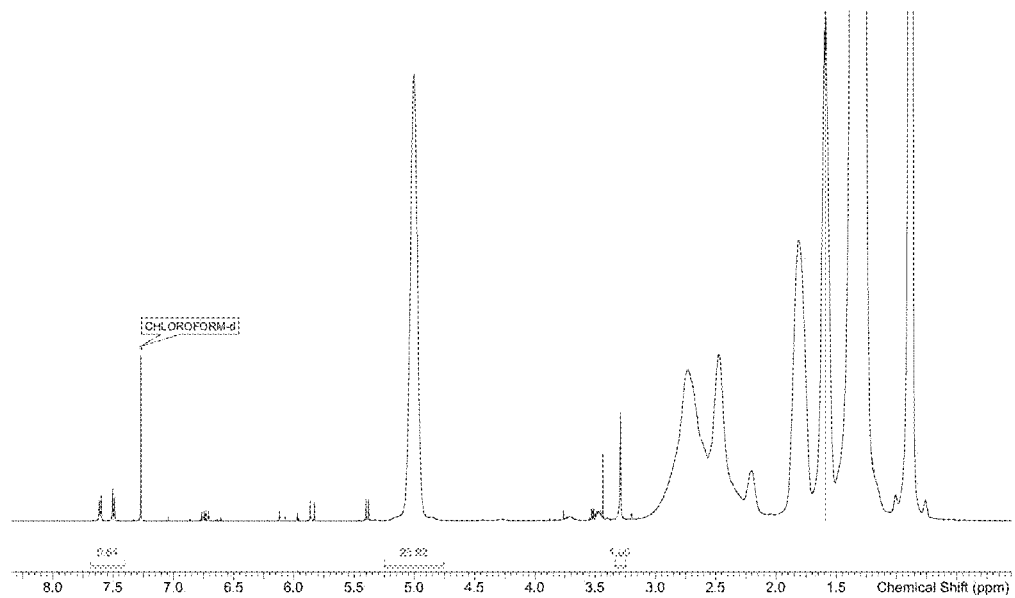
FIG. 3B illustrates the proton nuclear magnetic resonance spectroscopy data for the sample of 2.0% QUAT copolymer.

With reference to FIG. 3A and FIG. 3B, the structure of the resulting compound was evaluated using proton nuclear magnetic resonance ($^1$H NMR) spectroscopy. Samples of the antimicrobial adhesive copolymer compositions were prepared: one sample contained 0.2% QUAT and 99.8% 2oc by mole, the other sample contained 2% QUAT and 98% 2oc by mole. Each sample was dissolved using deuterated chloroform as a solvent. The samples of antimicrobial adhesive copolymer compositions were individually analyzed using a 500 MHz nuclear magnetic resonance (NMR) spectrometer, with each sample receiving 256 scans. The raw data from these scans were quantified and analyzed for signs of covalent polymerization. With reference to FIG. 4, the ratios of each monomer in the polymers were determined mathematically after identification of distinct QUAT-specific and cyanoacrylate-specific peaks. Such peaks were identified in part by referencing existing spectra for each of the known monomer samples.

Bactericidal and bacteriostatic effects of the antimicrobial adhesive copolymer compositions were investigated using *Staphylococcus epidermidis*, a Gram-positive organism, and *Escherichia coli*, a Gram-negative organism. Sterile glass tubes coated with antimicrobial adhesive copolymer composition samples (0.0%, 0.2%, 0.5%, 2.0%, and 5.0% QUAT by mole) were prepared, rinsed thoroughly with distilled water in order to remove any remaining QUAT monomer, and placed under UV for 20 mins to sterilize.

Figure 5:
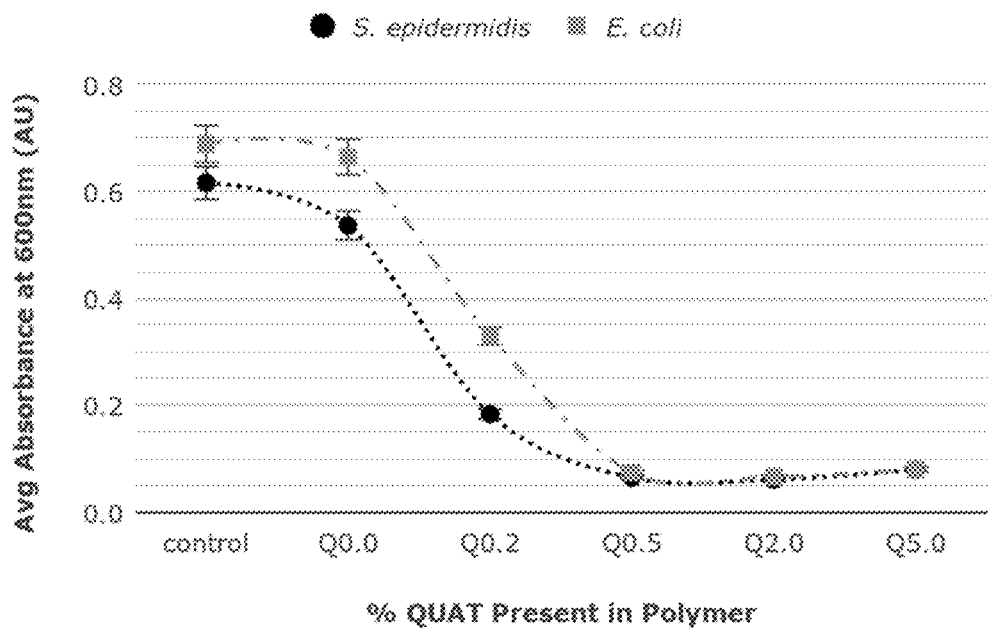
FIG. 5 illustrates the average absorbance of samples from the assays using an ultraviolet-visible spectrophotometer at 600 nm.

With reference to FIG. 5 and FIG. 6, each of the 36 sterile glass test tubes received 3 ml of sterile Mueller-Hinton broth and 40 µl of lag phase bacterial stock solution. Tubes were incubated at 34 C for 24 hours with constant agitation. At the 24-hour mark, 100 µl samples from each test tube were transferred to individual wells in a sterile 96-well transparent polystyrene round-bottom plate and the absorbance, or optical density, of each sample was measured at a wavelength of 600 nm ($OD_{600}$) of each sample was measured using ultraviolet-visible spectrophotometry. Raw data from these assays were averaged (see FIG. 6) and plotted on a graph in order to obtain a standard curve (see FIG. 5). This data was used to interpret the apparent bacteriostatic effects of the polymers over a 24-hour period.

Simultaneously, 36 sterile Petri dishes were prepared with fresh Mueller-Hinton agar. Each plate was labeled and inoculated with 40 µl of solution from the corresponding test tube after 24 hours of exposure to the test sample, then covered and incubated at 37° C. for 24 hours. These cultures were grown without any direct contact with the polymers past the initial 24-hour period, in order to determine whether exposure to the polymers in the first 24 hours would impact the viability of the cells post-exposure. At the 24-hour mark, plates were observed for signs of growth from each sample. All experimental methods were conducted in triplicate.

Cytotoxicity in cultured mammalian cells was assessed using mouse fibroblast cells from cell line NIH 3T3. The mouse fibroblast cells were maintained in Dulbecco's modified eagle medium (DMEM) with 10% fetal bovine serum (FBS) and 1% Penicillin/Streptomycin, at 37° C. and 5% CO2. A monolayer of the NIH 3T3 mouse fibroblast cells was seeded in each well of a 24-well plate at 5×10$^5$ cells/cm (subconfluent density) before incubating for 24 hours to allow the cells to become confluent. Small, flat pellets (approximately 1 cm in width) of the 0.2%, 2.0%, and 5.0% polymer samples were placed directly into the media. One row from each assay was intentionally kept free from polymer as a negative control. The plate was then left to incubate for 24 hours at 37° C., and cells were observed for morphological changes. The assay was repeated a total of 3 times.

The present disclosure demonstrates for the first time the successful covalent incorporation of QUAT monomers into a compatibly, antibacterial, cyanoacrylate-based polymer. There are a number of advantages associated with the immobilization of QUAT compounds within these polymers. Copolymerization of vinylbenzyl dimethyloctyl ammonium chloride monomers and 2-octyl cyanoacrylate monomers allows for optimal use of both molecules' properties. The present disclosure demonstrates that the resulting copolymer possesses both the antimicrobial properties of the QUAT monomers and the biocompatibility of the cyanoacrylate-based polymer. Due to this covalent incorporation, QUAT monomers are unable to leach from the polymer, which would lead to systemic toxicity and ultimately environmental contamination. This is vital as QUAT molecules are recognized as environmental toxins and hazards to marine life (see Â. S. Inácio et al., *Antimicrob. Agents Chemother.* 2013, 57, 2631; J. C. Cooper, *Ecotoxicol. Environ. Saf.* 1988, 16, 65; V. Di Nica et al., *Ecotoxicol. Environ. Saf.* 2017, 142, 567). Immobilization of such toxins by covalent interactions is a key theme in the field of green chemistry, and an advantage of the present disclosure.

With reference to FIG. 3A and FIG. 3B, the $^1$H NMR data support the hypothesis that copolymerization occurs between vinylbenzyl dimethyl octyl ammonium chloride and 2-octyl cyanoacrylate at room temperature. Reference peaks were identified by comparative analysis with the proposed molecular structure of the copolymer. Peak A at δ3.26 (s) represents the single benzylic proton which transforms from a vinylic proton in the QUAT monomer to a carbon backbone proton upon copolymerization. Peak A is shifted downfield as a result of deshielding from the strong electron withdrawing effect of the ammonium structure. Peak B at δ4.97 (s) represents the single CH—O proton within the ester group of the cyanoacrylate monomer. Peak C at δ7.59 (dd) represents the four aromatic protons present in each QUAT monomer. Peak C is broadened as a result of polymerization.

FIG. 3A depicts the $^1$H NMR spectrum obtained from the 0.2% QUAT copolymer sample in deuterated chloroform at 500 MHz (CDCl3, 500 MHz). Peak A is present with a relative integration value of 1.00, with δ3.26 (s, 1H); peak B is present with a relative integration value of 120.03, with δ4.97 (s, 1H); and peak C is present with a relative integration value of 0.62, with δ7.59 (dd, 4H).

FIG. 3B depicts the $^1$H NMR spectrum obtained from the 2% QUAT copolymer sample in deuterated chloroform at 500 MHz (CDCl3, 500 MHz). Peak A is present with a relative integration value of 1.00, with δ3.26 (s, 1H); peak B is present with a relative integration value of 25.92, with δ4.97 (s, 1H); and peak C is present with a relative integration value of 0.64, 67.59 (dd, 4H).

With reference to the peaks of interest in FIG. 3A and FIG. 3B, the C:B ratio indicates the ratio of QUAT:cyanoacrylate present. Peak C represents four protons while peaks B and A each represent one, thus, each proton represented by peak C possesses a relative integration value of 0.16 in both FIG. 3A and FIG. 3B. In FIG. 3A, the C:B ratio is approximately 0.0013, implying that the QUAT remaining in this polymer sample is 0.13% of the total polymer. As a molar equivalent of 0.2% was introduced to the initial reaction, the results from FIG. 3A indicate 65% QUAT incorporation. In FIG. 3B, the C:B ratio is approximately 0.0062, implying that the QUAT remaining in this polymer sample is 0.62% of the total polymer. As a molar equivalent of 2% was introduced to the initial reaction, the results from FIG. 3B indicate 31% QUAT incorporation.

To determine the bacterial toxicity of this QUAT-2oc copolymer, samples of 0.0% (2oc only, as the negative control), 0.2%, 0.5% 2.0%, and 5.0% QUAT were tested against liquid cultures of *S. epidermidis* and *E. coli*, as representative Gram-positive and Gram-negative species, respectively. Results from the antibacterial assays were obtained in triplicate, with three replicate experiments as described. Observations were made regarding apparent turbidity at the 24-hour mark of each repeat, and quantitative analysis of these tubes using UV-visible spectrophotometry confirmed these observations (FIG. 5 and FIG. 6). During the first round, the *S. epidermidis* bacteria-only controls and those exposed to 2oc-0.0% QUAT polymers appeared equally turbid, indicating robust bacterial growth (though one control contained a biofilm of *S. epidermidis* and was eliminated for that reason). All *S. epidermidis* tubes containing 0.2%, 0.5%, 2.0%, and 5.0% QUAT polymers each appeared transparent, indicating a lack of bacterial growth. Tubes containing *E. coli* positive controls as well as those containing *E. coli* and 2oc-0.0% QUAT polymers each appeared very turbid in all rounds, while tubes containing *E. coli* and 0.2% QUAT polymers appeared somewhat turbid. Tubes containing *E. coli* and 0.5%, 2.0%, and 5.0% QUAT polymers all appeared transparent, which was confirmed by quantitative analysis using UV-visible spectrophotometry (FIG. 5 and FIG. 6).

Data shown in FIG. 5 and FIG. 6 provide quantitative evidence to support the hypothesis that the QUAT-2oc copolymers substantially limit colony formation in both Gram-positive and Gram-negative organisms, while pure 2oc polymers do not. As demonstrated by the data obtained 0.2% QUAT, compared to the data obtained from 0.0% QUAT, the half maximal inhibitory concentration (IC50) of QUAT in the copolymer is no greater than 0.2% for both *Staphylococcus epidermidis* and *Escherichia coli* at 24 hours. There does not appear to be any enhancement of inhibitory properties when increasing the concentration of QUAT beyond 2.0%.

Figure 7:
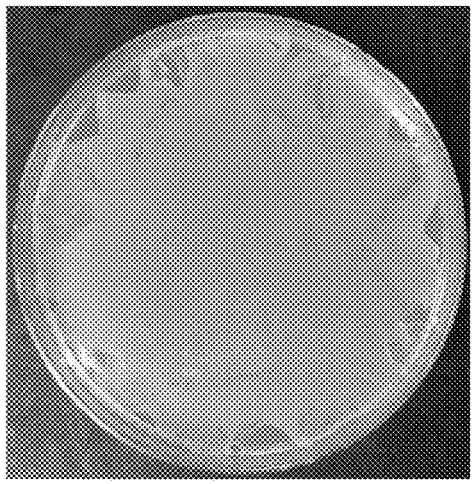
FIG. 7 presents six labeled black-and-white photographs of representative colony growth of S. epidermidis after exposure to the polymer.
Figure 7:
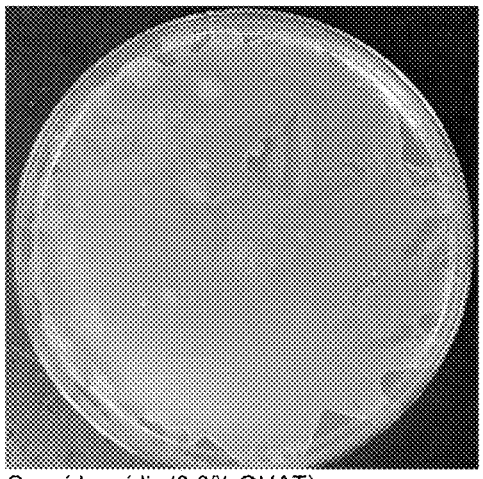
Figure 7:
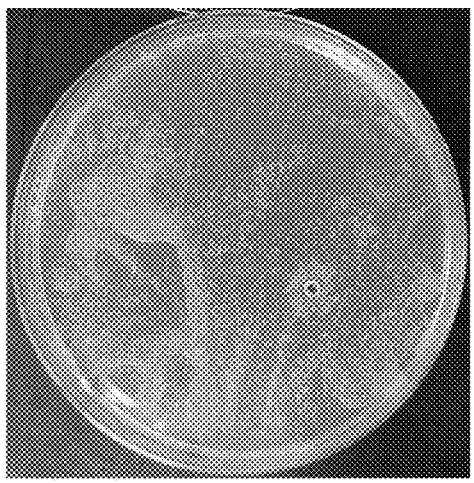
Figure 7:
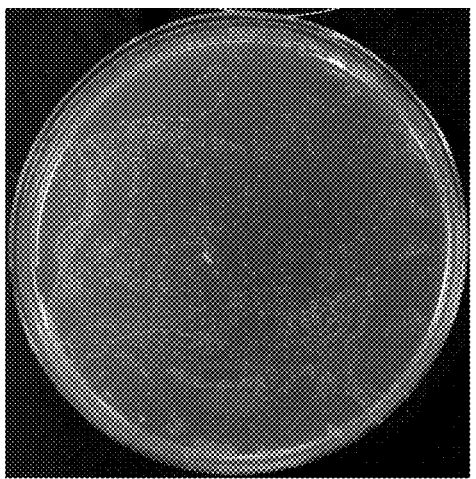
Figure 7:
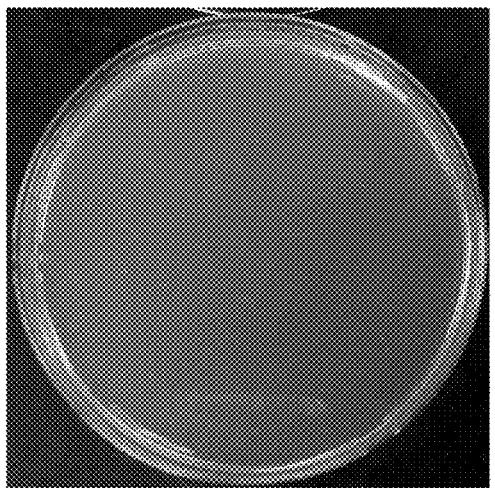
Figure 7:
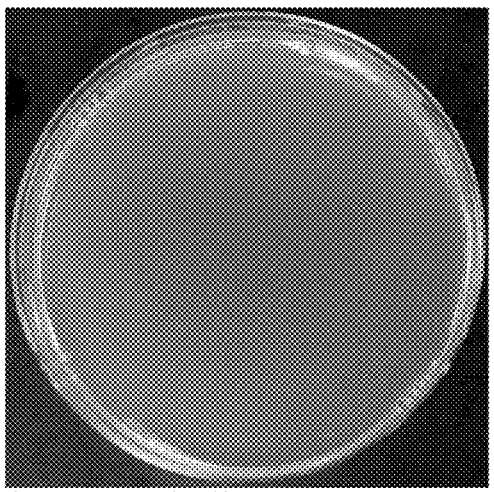

To evaluate whether the inhibitory effects were the result of bacteriostasis or bactericidal effects, isolates were grown on agar for an additional 24 hours to determine the postexposure cell viability in the absence of any polymer sample. After incubation at 37° C. for 24 hours, the petri dishes were observed and photographed, as shown in FIG. 7 (showing representative colony growth of *S. epidermidis*) and FIG. 8 (showing representative colony growth of *E. coli*). For both strains tested, colony growth was indistinguishable between the control and the samples that had been exposed to only 2oc, with all samples showing at least 90% lawn formation. 2oc-QUAT copolymer treatment was determined to be bactericidal, as *E. coli* colonies that had been exposed to the 0.2% copolymer showed a slight decrease in colony growth, while *S. epidermidis* showed less than 50% colonization. *E. coli* colonies that had been exposed to the 0.5% copolymer showed approximately 50% colonization, while *S. epidermidis* showed almost no bacterial growth. Upon exposure to the 2% and 5% copolymer, both strains examined showed no visible growth. Results were consistent in all plates through all rounds of experimentation. This qualitative data collected 24 hours after allowing colony growth on agar support the hypothesis that the 2oc-QUAT copolymers possess bactericidal properties via direct contact while pure 2oc polymers do not. This is evidenced by the inverse relationship between postexposure colony formation and concentration of QUAT present in the polymer during exposure. These observations suggest that the half maximal lethal concentration (LC50) of QUAT in the copolymer is approximately 0.2% for *Staphylococcus epidermidis* and approximately 0.5% for *Escherichia coli* at 24 hours.

The two antibacterial assays described here provide data which may seem to contradict observations made by Prince et al (2018), in which the authors observe a bacteriostatic effect from pure 2-octyl cyanoacrylate on Gram-positive species via a zone of inhibition assay. The zone of inhibition assay captures only the impact of diffused materials and allows for the unintended consequence of unincorporated cyanoacrylate monomers diffusing through the microbial lawn. Thus, it is possible that any observed bacteriostatic effect is simply a result of such diffusion rather than any effect brought on by cured polymers. This would not provide lasting protection from infection. Through our methods, and with reference to FIG. 5, FIG. 6, FIG. 7, and FIG. 8, we demonstrate no notable antimicrobial activity from the pure 2-octyl cyanoacrylate polymers. This finding is more in line with a study published by Romero et al (2009), which suggests that the polymerization event involving cyanoacrylates may kill some species of bacteria, but cured polymers lose this ability (see I. L. Romero et al., *Indian J. Ophthalmol.* 2009, 57, 341). By introducing QUAT materials to the cyanoacrylate-based polymers, these polymers become antimicrobial through a different mechanism, which is not dependent on diffusion and is effective against both Gram-positive and Gram-negative organisms (see F. F. Rossetti et al., *Int. J. Polym. Sci.* 2017, 1, 110).

The antimicrobial adhesive copolymer composition for wound closure, which encompasses surgical site closure, comprising cyanoacrylate-based tissue adhesive monomers and QUATs, may, in one aspect of the present disclosure, be in a chemical solution comprising i) a cyanoacrylate component, or a chemical component resulting from a reaction between a) a formaldehyde component and b) any cyanoacetate component or a cyanoacetic acid component; and ii) a charged quaternary ammonium component (QUAT) or a charged quaternary phosphonium component (QUPT), wherein the charged quaternary ammonium component or the charged quaternary phosphonium component comprises at least one reactive alkene group, which reactive alkene group may comprise at least one vinyl group. In another aspect, the antimicrobial adhesive copolymer compositions for wound closure may further comprise one or more of a plurality of charged quaternary ammonium components and/or one or more of a plurality of charged quaternary phosphonium components. A ratio of the cyanoacrylate component, or the chemical component resulting from a reaction between a formaldehyde component and a cyanoacetate component or a cyanoacetic acid component (together, the "CAC"), to the charged quaternary ammonium component or the charged quaternary phosphonium component, may be in a range of approximately 99.95% by mole cyanoacrylate component or CAC to 0.05% by mole charged quaternary ammonium component or charged quaternary phosphonium component, to approximately 90.0% by mole cyanoacrylate component or CAC to 10% by charged quaternary ammonium component or charged quaternary phosphonium component.

The cyanoacrylate component may be used in any absolute or relative amount, relative to the other components. The cyanoacrylate component may include, and may be selected from, but is not limited to, methyl cyanoacrylates, ethyl cyanoacrylates, butyl cyanoacrylates, and octyl cyanoacrylates, their derivatives, and mixtures thereof. The chemical component resulting from a reaction between a formaldehyde component and a cyanoacetate component or a cyanoacetic acid component may comprise one or more members of a group comprising methyl cyanoacrylates, ethyl cyanoacrylates, butyl cyanoacrylates, and octyl cyanoacrylates, their derivatives, and mixtures thereof The charged quaternary ammonium component may be used in any absolute or relative amount, relative to the other components. The charged quaternary ammonium component, characterized by the presence of at least one vinyl group, may include, and may be selected from, but is not limited to, (vinylbenzyl)dimethylalkylammonium chloride, (vinylbenzyl)trimethylammonium chloride, trimethyl(vinyl)ammonium chloride, and dimethylalkyl(vinyl)ammonium chloride, their derivatives, and mixtures thereof.

The charged quaternary phosphonium component may be used in any absolute or relative amount, relative to the other components. The charged quaternary phosphonium component, characterized by the presence of at least one vinyl group, may include, and may be selected from, but is not limited to, triphenyl(4-vinylbenzyl)phosphonium chloride, tri-n-butyl(4-vinylbenzyl)phosphonium chloride, benzyl(vinyl)phosphonium chloride, trimethyl(4-vinylbenzyl)phosphonium chloride, and (formylmethyl)triphenylphosphonium chloride, their derivatives, and mixtures thereof.

The copolymer comprising cyanoacrylate-based tissue adhesive monomers and QUATs and/or QUPTs may, in one aspect of the present disclosure, be a polymer obtained by a process comprising the steps of combining: i) a cyanoacrylate component or any chemical component resulting from a reaction between a) a formaldehyde component and b) any cyanoacetate component or cyanoacetic acid component; and ii) a charged quaternary ammonium component or a charged quaternary phosphonium component, wherein the charged quaternary ammonium component or the charged quaternary phosphonium component contains at least one vinyl group.

The antimicrobial adhesive copolymer compositions for wound closure, which encompasses surgical site closure, may be used in a method for the treatment or prevention of infection at a wound site or a surgical site comprising adhering the wound site or surgical site closed or partially closed with, or injecting or placing into the wound site or surgical site, a chemical solution comprising i) a cyanoacrylate component, or a chemical component resulting from a reaction between a) a formaldehyde component and b) any cyanoacetate component or a cyanoacetic acid component; and ii) a charged quaternary ammonium component (QUAT) or a charged quaternary phosphonium component (QUPT). The chemical solution used in the method may comprise a plurality of charged quaternary ammonium components and/or a plurality of charged quaternary phosphonium components.

When combined together at room temperature, cyanoacrylate monomers undergo an exothermic reaction with positively-charged quaternary ammonium compounds or positively-charged quaternary phosphonium compounds that contain a vinyl functional group. This reaction results in the immobilization of the quaternary ammonium compounds or quaternary phosphonium compounds. The resulting product demonstrates broad-spectrum bacteriostatic properties and bactericidal properties, and does not demonstrate cytotoxicity in cultured mammalian tissue.

Potential cytotoxic effects of the copolymers were investigated using a direct contact cell viability assay, where polymer samples were placed directly into the cell growth medium. A lack of cellular morphological changes, and no evidence of cell death, would support the hypothesis that no toxic materials leach from the polymers into the culture system. The described assay is also useful for determining toxicity of the polymer itself upon contact with viable mammalian cells, and thus its potential to cause localized irritation when applied to the tissue.

Figure 8:
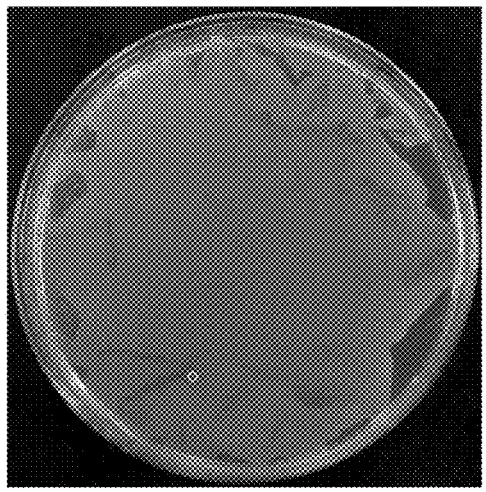
FIG. 8 presents six labeled black-and-white photographs of representative colony growth of E. coli after exposure to the polymer.
Figure 8:
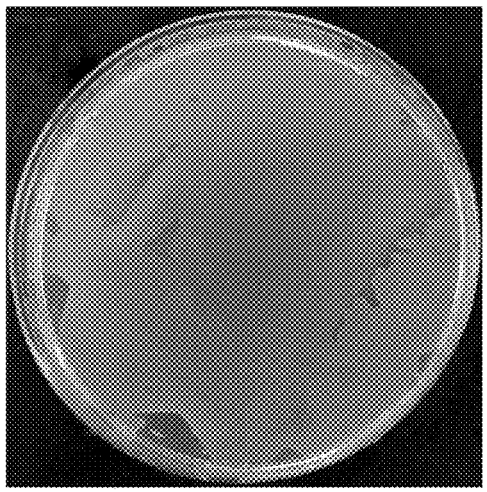
Figure 8:
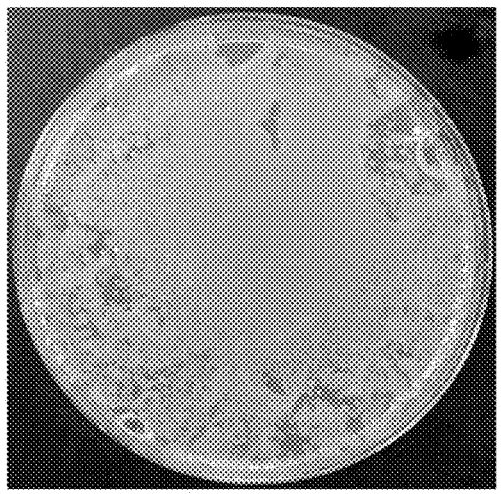
Figure 8:
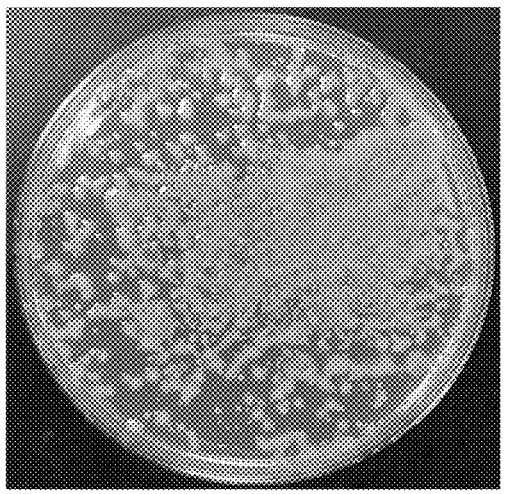
Figure 8:
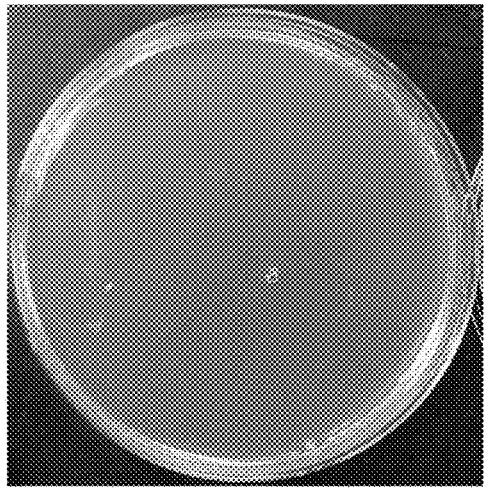
Figure 8:
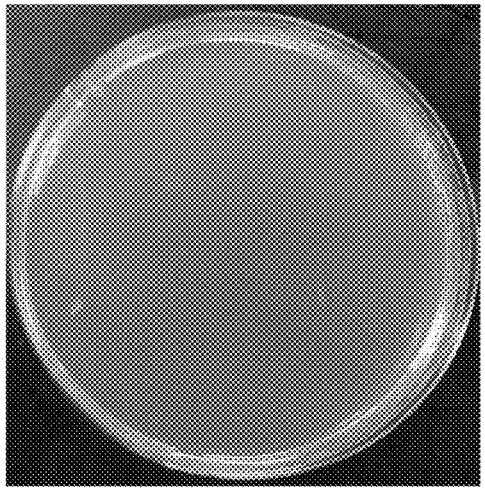
Figure 9:
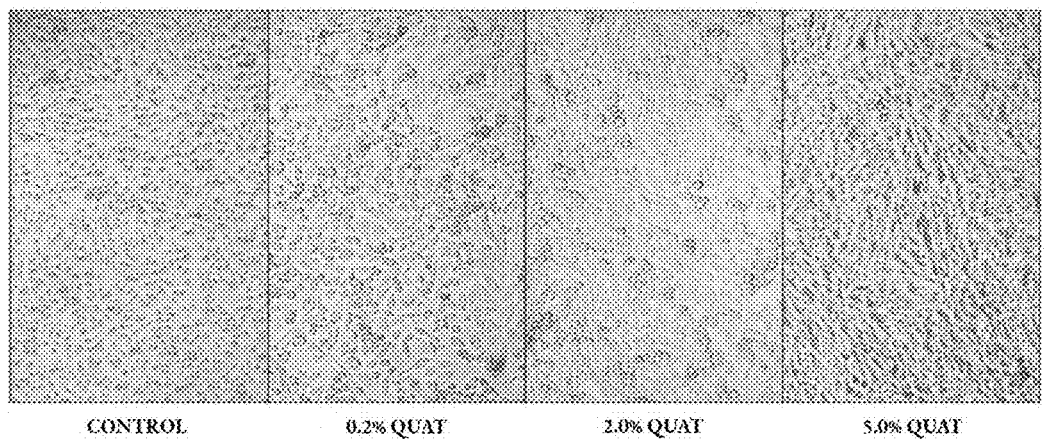
FIG. 9 presents four labeled representative micrographs, at 100× magnification, from wells across the three direct contact cell viability experiments.

With reference to FIG. 8, images at 100× magnification of each well of cultured mouse 3T3 fibroblasts were captured after 24 hours of incubation at 37° C. and 5% CO2, showing in FIG. 9, left to right, a negative control; control; 0.2% copolymer; 2% copolymer; and 5% copolymer. All wells contained morphologically normal cells at greater than 50% confluence after 24 hours. Control cells were indistinguishable from those treated with CA-QUAT copolymer, indicating undetectable levels of cell death. Cells treated with soluble QUAT only showed near complete death after 24 hours (data not shown). Fibroblast cells are considered to be morphologically normal when they are bipolar or multipolar, are elongated or triangular in shape, contain visible nuclei, and remain adhered to a substrate even after gentle rinsing. The vast majority of cells should be free from granularity around the nucleus and cytoplasmic vacuolation. Since the unique shape of fibroblast cells come from their adhesion to a surface and to surrounding cells, it is quite easy to recognize a fibroblast cell which is no longer adhered, because they will take on a round or spherical shape.

Biocompatibility of the 2oc-QUAT copolymers is evidenced by qualitative data collected during the described cell viability assay. QUAT toxicity in mammalian tissue has been reported in the literature (see, e.g., A. S. Inácio et al., Antimicrob. Agents Chemother. 2013, 57, 2631; R. F. El-Hayek, K. Dye, J. C. Warner, J. Biomed. Mater. Res. Part A 2006, 79A, 874; H. L. Shane et al., J. Immunotoxicol. 2017, 14, 204). Thus, diffusion of QUAT monomers through or into the surrounding media would likely lead to cell death. Little to no apparent cytotoxicity was demonstrated by direct contact cytotoxicity assays, as is visible in FIG. 9. This supports the hypothesis that the described polymers are not toxic to mammalian cells on contact. When grown in media that contains solid samples of each polymer, NIH 3T3 mouse fibroblasts did not undergo any notable morphological changes that would indicate toxicity.

Cyanoacrylates have been explored as potential mechanisms for drug delivery and used as a means for suspension of antimicrobial agents, such as polyvinylpyrrolidone iodine complex and phenols. The present disclosure teaches covalent copolymerization of cyanoacrylates with quaternary ammonium salts. Importantly, the 2oc-QUAT copolymer is both bacteriostatic and bactericidal against both Gram positive (*S. epiderimidis*) and Gram negative (*E. coli*) bacteria, demonstrating that antibacterial properties are indeed retained upon polymerization. For medical applications, it is important that toxicity is directed only toward prokaryotes, and not the eukaryotic (human) host. Therefore, the lack of any detectable toxicity to mammalian cells in the cell culture assay is a strong indication that 2oc-QUAT is biocompatible with human tissue, with advantageous rapid polymerization, biocompatibility, and antibacterial properties of the adhesive copolymer of the present disclosure.

Certain aspects of the present disclosure were described above. From the foregoing it will be seen that this disclosure is one well adapted to attain all the ends and objects set forth above, together with other advantages, which are obvious and inherent to the compounds of the present disclosure. It will be understood that certain features and sub-combinations are of utility and may be employed without reference to other features and sub-combinations. It is expressly noted that the present disclosure is not limited to those aspects described above, but rather the intention is that additions and modifications to what was expressly described herein are also included within the scope of the disclosure. Moreover, it is to be understood that the features of the various aspects described herein are not mutually exclusive and can exist in various combinations and permutations, even if such combinations or permutations were not made express herein, without departing from the spirit and scope of the disclosure. In fact, variations, modifications, and other implementations of what was described herein will occur to those of ordinary skill in the art without departing from the spirit and the scope of the disclosure. As such, the disclosure is not to be defined only by the preceding illustrative description.

Accordingly, what is claimed is:

1. An antimicrobial adhesive copolymer composition for wound closure, comprising:
   a cyanoacrylate component; and
   a charged quaternary ammonium component or a charged quaternary phosphonium component, wherein the charged quaternary ammonium component or the charged quaternary phosphonium component comprises at least one reactive alkene group, and alkyl group of the charged quaternary ammonium component or charged quaternary phosphonium component is $C_nH_{2n+1}$, where n ranges from 4 to 18.

2. The antimicrobial adhesive copolymer composition for wound closure of claim 1, wherein the cyanoacrylate component is selected from a group comprising methyl cyanoacrylates, ethyl cyanoacrylates, butyl cyanoacrylates, and octyl cyanoacrylates, their derivatives, and mixtures thereof.

3. The antimicrobial adhesive copolymer composition for wound closure of claim 1, wherein the at least one reactive alkene group comprises at least one vinyl group.

4. The antimicrobial adhesive copolymer composition for wound closure of claim 1, wherein the charged quaternary ammonium component is selected from a group comprising vinylbenzyldimethylalkylammonium chloride, and dimethylalkylvinylammonium chloride, their derivatives, and mixtures thereof, and wherein the alkyl group of the charged quaternary ammonium component is $C_nH_{2n+1}$, where n ranges from 8 to 18.

5. A process for covalent copolymerization of cyanoacrylates with quaternary ammonium salts to create the antimicrobial adhesive copolymer composition for wound closure of claim 4, the process comprising auto-polymerization of cyanoacrylates utilizing an amino acid or a hydroxide ion as a nucleophile; initiation of copolymerization wherein the nucleophile attacks a vinylic carbon, breaking a vinylic bond and generating an anionic charge on a central carbon atom of a cyanoacrylate monomer; and wherein a central carbon atom then acts as a nucleophile, inducing a chain of nucleophilic attacks on the remaining cyanoacrylate monomers.

6. The antimicrobial adhesive copolymer composition for wound closure of claim 1, wherein the charged quaternary phosphonium component is selected from a group comprising dimethylalkyl-4-vinylbenzyl phosphonium chloride, vinylbenzyldimethylalkylphosphonium chloride, and tri-n-butyl-4-vinylbenzylphosphonium chloride, their derivatives, and mixtures thereof, and wherein the alkyl group of the charged quaternary phosphonium component is $C_nH_{2n+1}$, where n ranges from 8 to 18.

7. A process for covalent copolymerization of cyanoacrylates with quaternary ammonium salts to create the antimicrobial adhesive copolymer composition for wound closure of claim 6, the process comprising auto-polymerization of cyanoacrylates utilizing an amino acid or a hydroxide ion as a nucleophile; initiation of copolymerization wherein the nucleophile attacks a vinylic carbon, breaking a vinylic bond and generating an anionic charge on a central carbon atom of a cyanoacrylate monomer; and wherein the central carbon atom then acts as a nucleophile, inducing a chain of nucleophilic attacks on the remaining cyanoacrylate monomers.

8. The antimicrobial adhesive copolymer composition for wound closure of claim 1, wherein the antimicrobial adhesive copolymer composition further comprises more than the one charged quaternary ammonium components and/or further comprises more than the one charged quaternary phosphonium components, and wherein the alkyl group of the charged quaternary ammonium component, or the alkyl group of the charged quaternary phosphonium component, component is $C_nH_{2n+1}$, where n ranges from 8 to 18.

9. A process for covalent copolymerization of cyanoacrylates with quaternary ammonium salts to create the antimicrobial adhesive copolymer composition for wound closure of claim 8, the process comprising auto-polymerization of cyanoacrylates utilizing an amino acid or a hydroxide ion as a nucleophile; initiation of copolymerization wherein the nucleophile attacks a vinylic carbon, breaking a vinylic bond and generating an anionic charge on a central carbon atom of a cyanoacrylate monomer; and wherein the central carbon atom then acts as a nucleophile, inducing a chain of nucleophilic attacks on the remaining cyanoacrylate monomers.

10. The antimicrobial adhesive copolymer composition for wound closure of claim 1, wherein a ratio of the cyanoacrylate component to the charged quaternary ammonium component or the charged quaternary phosphonium component is in a range of approximately 99.95% by mole cyanoacrylate component to 0.05% by mole charged quaternary ammonium component or charged quaternary phosphonium component, to approximately 90.0% by mole cyanoacrylate component to 10% by charged quaternary ammonium component or charged quaternary phosphonium component.

* * * * *